(12) United States Patent
Shimamoto

(10) Patent No.: US 10,359,625 B2
(45) Date of Patent: Jul. 23, 2019

(54) METHOD FOR SETTING DRIVING CONDITIONS AND APPARATUS FOR SETTING DRIVING CONDITIONS OF OPTICAL SCANNING APPARATUS

(71) Applicant: OLYMPUS CORPORATION, Tokyo (JP)

(72) Inventor: Atsuyoshi Shimamoto, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 79 days.

(21) Appl. No.: 15/708,781

(22) Filed: Sep. 19, 2017

(65) Prior Publication Data

US 2018/0003954 A1 Jan. 4, 2018

Related U.S. Application Data

(63) Continuation of application No. PCT/JP2015/001832, filed on Mar. 30, 2015.

(51) Int. Cl.
*G02B 26/10* (2006.01)
*G02B 23/24* (2006.01)
*A61B 1/00* (2006.01)

(52) U.S. Cl.
CPC ........ *G02B 26/103* (2013.01); *A61B 1/00006* (2013.01); *A61B 1/00172* (2013.01); *G02B 23/2469* (2013.01); *G02B 26/101* (2013.01)

(58) Field of Classification Search
None
See application file for complete search history.

(56) References Cited

U.S. PATENT DOCUMENTS

2006/0013528 A1* 1/2006 Rosman ............... B82Y 35/00
385/25
2008/0297868 A1* 12/2008 Mizumoto ......... G02B 26/0858
359/199.1
(Continued)

FOREIGN PATENT DOCUMENTS

JP 5190267 B2 2/2013
JP 2014-147462 A 8/2014
JP 2014-198089 A 10/2014

OTHER PUBLICATIONS

International Search Report dated Jun. 16, 2015 received in International Application No. PCT/JP2015/001832, together with an English-language translation.
(Continued)

*Primary Examiner* — Fernando Alcon
(74) *Attorney, Agent, or Firm* — Scully, Scott, Murphy & Presser, P.C.

(57) ABSTRACT

A method and an apparatus for setting driving conditions applied in an optical scanning apparatus. The method for setting driving conditions includes attaching a scanning pattern detector and adjusting a scanning pattern detected by the scanning pattern detector by changing a drive signal applied to an actuator (steps S03 to S06). The step of adjusting includes setting a first drive signal value of the drive signal applied to the actuator and a target amplitude of the scanning pattern (step S03) and determining a frequency of the drive signal applied to the actuator by comparing an amplitude of the scanning pattern detected by changing the frequency of the drive signal applied to the actuator with the target amplitude while vibrating the actuator at the first drive signal value (step S04).

16 Claims, 13 Drawing Sheets

(56) References Cited

U.S. PATENT DOCUMENTS

| | | | |
|---|---|---|---|
| 2009/0177042 A1* | 7/2009 | Johnston | A61B 1/00172 600/178 |
| 2009/0316116 A1* | 12/2009 | Melville | A61B 1/0008 353/31 |
| 2011/0122101 A1* | 5/2011 | Kurozuka | G02B 26/101 345/204 |
| 2012/0224235 A1* | 9/2012 | Hanada | G02B 26/0841 358/474 |
| 2016/0143515 A1* | 5/2016 | Shimamoto | A61B 1/00006 600/106 |
| 2017/0311776 A1* | 11/2017 | Shimamoto | A61B 1/00 |
| 2018/0113298 A1* | 4/2018 | Shimamoto | A61B 1/00006 |
| 2018/0196250 A1* | 7/2018 | Shimamoto | A61B 1/00 |

OTHER PUBLICATIONS

Japanese Office Action dated Mar. 19, 2019 in Japanese Patent Application No. 2017-508794.
Chinese Office Action dated Apr. 18, 2019 in Chinese Patent Application No. 201580078280.0.

* cited by examiner

Number of revolutions

Number of revolutions

METHOD FOR SETTING DRIVING CONDITIONS AND APPARATUS FOR SETTING DRIVING CONDITIONS OF OPTICAL SCANNING APPARATUS

CROSS-REFERENCE TO RELATED APPLICATION

The present application is a Continuing Application based on International Application PCT/JP2015/001832 filed on Mar. 30, 2015, the content of which is incorporated herein by reference.

TECHNICAL FIELD

This disclosure relates to a method for setting driving conditions and an apparatus for setting driving conditions for an optical scanning apparatus.

BACKGROUND

Optical scanning apparatuses that vibrate an optical fiber for guiding light from a light source, such as a laser, and scan emitted light over an object in a spiral pattern have been proposed (for example, see JP 5190267 B2 (PTL 1) and JP 2014-147462 A (PTL 2)). In such optical scanning apparatuses, the tip of the optical fiber is supported at one end in a vibratable state and is driven in two axial directions, orthogonal to the optical axis of the optical fiber and orthogonal to each other, by a drive mechanism that uses piezoelectric elements or electromagnetic means. By shifting the phase of vibration in the two orthogonal axial directions by 90° from each other, vibrating at the same frequency, and causing the amplitude of vibration to rise and fall periodically between zero and the maximum, the object can be scanned over a spiral scanning pattern. Such a spiral scanning pattern is also referred to as a spiral scan.

The frequency producing vibration in the optical fiber of an optical scanning apparatus is often set near the resonance frequency of the tip of the optical fiber. The reason is that setting the driving frequency near the resonance frequency allows scanning at a larger amplitude with less energy. For example, PTL 2 discloses a method for using an optical position detector, such as a Position Sensitive Detector (PSD), to detect the scanning pattern of a spiral scan and for adjusting the driving parameters, such as the amplitude, phase difference, and driving frequency, of the applied voltage so that the outermost periphery is approximately shaped as a true circle. The driving frequency is set to the frequency that maximizes the amplitude of the fiber, i.e. the resonance frequency.

CITATION LIST

Patent Literature

PTL 1: JP 5190267 B2
PTL 2: JP 2014-147462 A

SUMMARY

A method according to this disclosure is for setting driving conditions applied in an optical scanning apparatus comprising an optical fiber that guides light from a light source and emits the light from a tip supported vibratably and an actuator that vibrates the tip of the optical fiber, the method comprising:

attaching a scanning pattern detector configured to detect a scanning pattern of the light emitted from the tip of the optical fiber; and
adjusting the scanning pattern detected by the scanning pattern detector by applying a drive signal to the actuator to vibrate the tip and changing the drive signal,
wherein the step of adjusting comprises
setting a first drive signal value of the drive signal applied to the actuator and a target amplitude of the scanning pattern; and
determining a frequency of the drive signal applied to the actuator by comparing an amplitude of the scanning pattern detected by changing the frequency of the drive signal applied to the actuator with the target amplitude while vibrating the actuator at the first drive signal value.

In the step of determining the frequency, the frequency of the drive signal applied to the actuator is preferably changed towards a resonance frequency of the tip of the optical fiber from an initial value that is a frequency separated from the resonance frequency by a predetermined value.

The actuator is preferably configured to be capable of vibrating the optical fiber in a first direction and a second direction that are orthogonal to each other and are orthogonal to an emission direction of the light at the tip of the optical fiber, and the method preferably further comprises determining, after the frequency of the drive signal is determined for vibration in the first direction in the step of determining the frequency, a second drive signal value applied to the actuator by comparing an amplitude of the scanning pattern detected by changing the drive signal applied to the actuator in the second direction with the target amplitude while vibrating the actuator in the second direction at the determined frequency.

The step of determining the second drive signal value is preferably performed so that an amplitude of the drive signal in the second direction does not exceed a predetermined value.

The step of adjusting preferably comprises adjusting phase by adjusting a phase difference, after the step of determining the second drive signal value, between a drive signal in the first direction and a drive signal in the second direction so that an ellipticity $\gamma=b/a$ exceeds a predetermined value, where a is a long radius and b is a short radius of a peripheral shape of the scanning pattern detected by the scanning pattern detector when, at the frequency determined in the step of determining the frequency, a drive signal at the first drive signal value is applied to the actuator in the first direction and a drive signal at the second drive signal value is applied to the actuator in the second direction. Alternatively, the step of adjusting may comprise adjusting phase by adjusting a phase difference, after the step of determining the second drive signal value, between a drive signal in the first direction and a drive signal in the second direction so that an ellipticity $\gamma=b/a$ exceeds a predetermined value, where a is a long radius and b is a short radius of an outermost peripheral shape of the scanning pattern detected by the scanning pattern detector when, at the frequency determined in the step of determining the frequency, a drive signal taking the first drive signal value as a maximum value of amplitude is applied to the actuator in the first direction and a drive signal taking the second drive signal value as a maximum value of amplitude is applied to the actuator in the second direction to cause the tip of the optical fiber to scan in a spiral.

The method may further comprise testing an amplitude convergence rate after the step of adjusting phase, the amplitude convergence rate being a value obtained by dividing a minimum amplitude by a maximum amplitude of the scanning pattern detected by the scanning pattern detector when applying a drive signal to the actuator to cause the tip of the optical fiber to scan in a spiral, the drive signal taking the first drive signal value as a maximum value of amplitude in the first direction and taking the second drive signal value as a maximum value of amplitude in the second direction.

The method preferably further comprises storing, in a memory of the optical scanning apparatus, the frequency of the drive signal determined in the step of determining the frequency, the first drive signal value set in the step of setting, the second drive signal value set in the step of determining the second drive signal value, and the phase difference adjusted in the step of adjusting phase.

The optical scanning apparatus may be an optical scanning endoscope.

An apparatus according to this disclosure for setting driving conditions is applied in an optical scanning apparatus comprising an optical fiber that guides light from a light source and emits the light from a tip supported vibratably and an actuator that vibrates the tip of the optical fiber, the apparatus for setting driving conditions comprising:

a controller configured to control the actuator; and a scanning pattern detector configured to detect a scanning pattern of the light emitted from the tip of the optical fiber, wherein the controller adjusts the scanning pattern detected by the scanning pattern detector by applying a drive signal to the actuator to vibrate the tip and changing the drive signal, the controller adjusting the scanning pattern by setting a first drive signal value of the drive signal applied to the actuator and a target amplitude of the scanning pattern and then determining a frequency of the drive signal applied to the actuator by comparing an amplitude of the scanning pattern detected by changing the frequency of the drive signal applied to the actuator with the target amplitude while vibrating the actuator at the first drive signal value.

The controller preferably determines the frequency of the drive signal applied to the actuator by changing the frequency of the drive signal applied to the actuator towards a resonance frequency of the tip of the optical fiber from an initial value that is a frequency separated from the resonance frequency by a predetermined value.

The actuator is preferably configured to be capable of vibrating the optical fiber in a first direction and a second direction that are orthogonal to each other and are orthogonal to an emission direction of the light at the tip of the optical fiber, and the controller is preferably configured to, after determining the frequency of the drive signal for vibration in the first direction, determine a second drive signal value applied to the actuator by comparing an amplitude in the second direction of the scanning pattern detected by changing the drive signal applied to the actuator in the second direction with the target amplitude while vibrating the actuator in the second direction at the determined frequency.

The controller is preferably configured to, after determining the second drive signal value, adjust a phase difference between a drive signal in the first direction and a drive signal in the second direction so that an ellipticity $\gamma=b/a$ exceeds a predetermined value, where a is a long radius and b is a short radius of a peripheral shape of the scanning pattern detected by the scanning pattern detector when, at the determined frequency, a drive signal at the first drive signal value is applied to the actuator in the first direction and a drive signal at the second drive signal value is applied to the actuator in the second direction. Alternatively, the controller may be configured to, after determining the second drive signal value, adjust a phase difference between a drive signal in the first direction and a drive signal in the second direction so that an ellipticity $\gamma=b/a$ exceeds a predetermined value, where a is a long radius and b is a short radius of an outermost peripheral shape of the scanning pattern detected by the scanning pattern detector when, at the determined frequency, a drive signal taking the first drive signal value as a maximum value of amplitude is applied to the actuator in the first direction and a drive signal taking the second drive signal value as a maximum value of amplitude is applied to the actuator in the second direction to cause the tip of the optical fiber to scan in a spiral.

The controller is preferably configured to, after adjusting the phase difference, test an amplitude convergence rate that is a value obtained by dividing a minimum amplitude by a maximum amplitude of the scanning pattern detected by the scanning pattern detector when applying a drive signal to the actuator to cause the tip of the optical fiber to scan in a spiral, the drive signal taking the first drive signal value as a maximum value of amplitude in the first direction and taking the second drive signal value as a maximum value of amplitude in the second direction.

The apparatus for setting driving conditions preferably stores, in a memory of the optical scanning apparatus, the frequency of the drive signal, the first drive signal value, the second drive signal value, and the phase difference.

In this application, the "scanning pattern detector" is means for two-dimensionally detecting the scanning pattern of light projected by vibration of an optical fiber. For example, an image sensor such as a Position Sensitive Detector (PSD) or a Charge Coupled Device (CCD) may be used as the scanning pattern detector. Alternatively, a method for projecting the scanning pattern on a screen and recognizing the scanning pattern with a human eye may be used as the scanning pattern detector. The scanning pattern detector may also be a detector, disposed inside the optical scanning apparatus, that detects the position of the tip of the optical fiber. The "optical scanning apparatus" is a scanning apparatus that vibrates the tip of an optical fiber to scan an object. Examples of the optical scanning apparatus also include a wide-angle optical system that irradiates light over a wider region than the amplitude of the optical fiber, such as an optical scanning endoscope or an optical scanning projector, and a narrow-focus optical system in which the range over which light is projected is narrower than the amplitude of the optical fiber, such as an optical scanning microscope. The "first drive signal value" and the "second drive signal value" represent the amplitude of the drive signal. For example, when driving a piezoelectric element, these signal values are the amplitudes of the vibration voltage.

BRIEF DESCRIPTION OF THE DRAWINGS

In the accompanying drawings:

FIG. 3A is a side view, and FIG. 3B is a cross-section along the A-A line in FIG. 3A;

FIG. 13A illustrates the maximum amplitude ($h_{max}$), and FIG. 13B illustrates the minimum amplitude ($h_{min}$).

DETAILED DESCRIPTION

Upon examination, we discovered that in a fiber-scanning type optical scanning apparatus that scans with an optical fiber, vibrating the tip of the optical fiber at the resonance frequency causes the vibration not to converge sufficiently at the central portion of the spiral scan, increasing the likelihood of an unscanned portion in the scanning area. Also, driving at the resonance frequency makes it easy for the scanning pattern to be distorted into an ellipse and for the amplitude to decrease upon even a small change in the resonance frequency caused by a change in the environment, such as a change in temperature. Therefore, the tip of the optical fiber is preferably vibrated at a frequency slightly distant from the resonance frequency. However, upon shifting the driving frequency by an appropriate value from the resonance frequency of the fiber tip, the amplitude of the fiber tip decreases, the scanning range shrinks, and energy efficiency deteriorates. Furthermore, upon increasing the voltage or current applied to the drive mechanism while the driving frequency is too far from the resonance frequency, the drive mechanism may malfunction or be damaged.

In light of these considerations, it would be helpful to provide a method and apparatus for setting appropriate driving conditions in an optical scanning apparatus.

Embodiments of this disclosure are described below with reference to the drawings.

Embodiment 1

Figure 1:
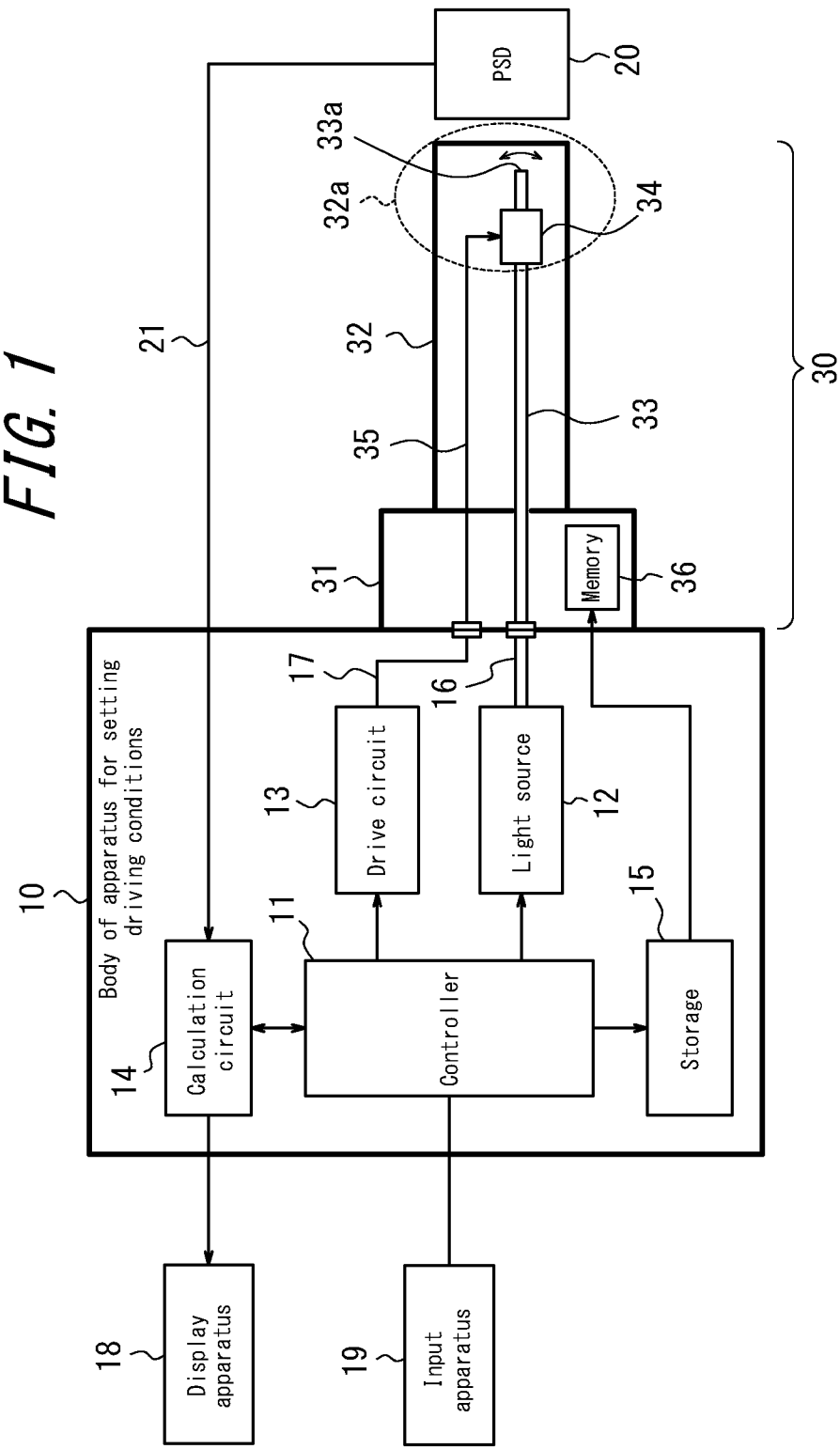
FIG. 1 is a block diagram illustrating an optical scanning endoscope connected to an apparatus for setting driving conditions according to Embodiment 1.

FIG. 1 is a block diagram illustrating an optical scanning endoscope 30 (optical scanning apparatus) connected to an apparatus for setting driving conditions according to Embodiment 1 of this disclosure. The apparatus for setting driving conditions includes a body 10 of the apparatus for setting driving conditions and a PSD 20 (scanning pattern detector). As necessary, a display apparatus 18 such as a display and an input apparatus 19 such as a keyboard, mouse, and/or touch panel are connected to the body 10 of the apparatus for setting driving conditions. The optical scanning endoscope 30 is connected to the body 10 of the apparatus for setting driving conditions by a connector 31. The PSD 20 is a detector for detecting the position of an optical spot on a detection surface and outputs a voltage value corresponding to the coordinates of the spot position as a detection signal.

The optical scanning endoscope 30 that is subjected to setting of driving conditions is the scope portion of an endoscope apparatus and includes an optical fiber 33 for illumination (optical fiber) inserted through the optical scanning endoscope 30, an actuator 34 that vibrates a tip 33a of the optical fiber 33 for illumination, a drive signal wire 35 that transmits drive signals to the actuator 34, and a memory 36 embedded inside the optical scanning endoscope 30 (for example, in the connector 31). Optical fibers 37 for receiving light (see FIG. 2) are inserted through the optical scanning endoscope 30 and receive and propagate light to be detected, such as reflected light and fluorescent light yielded by irradiation of illumination light.

During endoscopic observation, the optical scanning endoscope 30 is connected to a control apparatus body of an optical scanning endoscope apparatus by the connector 31 and is used to generate an endoscopic image. The optical scanning endoscope apparatus body includes components such as a light source that supplies light to the optical scanning endoscope 30, a drive circuit for driving the actuator 34, and an image processing circuit that generates an image from pixel data received by the optical scanning endoscope 30. Such an optical scanning endoscope apparatus is, for example, disclosed in JP 2014-44265 A and JP 2014-145941 A. The optical scanning endoscope 30 is usually commercially distributed separately from the control apparatus body, and the apparatus for setting driving conditions of this disclosure is mainly for setting driving conditions of the optical scanning endoscope 30 at the time of product shipment.

Like the control apparatus body during endoscopic observation, the body 10 of the apparatus for setting driving conditions is configured to be connectable to the connector 31 of the optical scanning endoscope 30. The body 10 of the apparatus for setting driving conditions includes a controller 11 that controls the body 10 of the apparatus for setting driving conditions overall, a light source 12 that supplies illumination light for setting driving conditions to the optical scanning endoscope 30, a drive circuit 13 that drives the actuator 34 of the optical scanning endoscope 30, a calculation circuit 14 that receives and processes output from the PSD 20, and a storage 15 that stores driving parameters indicating driving conditions output from the calculation circuit 14.

The light source 12 includes a light source such as a laser diode or a Diode-Pumped Solid-State (DPSS) laser. When performing endoscopic observation with the optical scanning endoscope 30, a plurality of light sources that emit light of different wavelengths may be used to obtain a color image, but it suffices for the body 10 of the apparatus for setting driving conditions to include at least one light source for setting driving conditions. The light emission timing of the light source 12 is controlled by the controller 11. Light emitted from the light source 12 is incident on the optical fiber 16 for illumination and combined onto the optical fiber 33 for illumination of the optical scanning endoscope 30 between the housing of the body 10 of the apparatus for setting driving conditions and the connector 31 of the optical scanning endoscope 30. Single-mode optical fibers, for example, may be used as the optical fibers 16, 33 for illumination.

The drive circuit 13 supplies a similar drive signal to the actuator 34 of the optical scanning endoscope 30 as during endoscopic observation. As described below, when the tip 33a of the optical fiber 33 for illumination is driven by piezoelectric elements, the drive circuit 13 supplies driving voltage to the piezoelectric elements. The output of the drive circuit 13 is supplied to the drive signal wire 17. The drive signal wire 17 is connected to the drive signal wire 35 of the optical scanning endoscope 30 between the housing of the body 10 of the apparatus for setting driving conditions and the connector 31 of the optical scanning endoscope 30. The timing at which driving of the drive circuit 13 starts is also controlled by the controller 11.

Over a detection signal wire 21, the calculation circuit 14 acquires a detection signal that is output by the PSD 20 and corresponds to the illumination position of illumination light on the light receiving surface. The calculation circuit 14 then converts the detection signal to the coordinates (x, y) of the illumination position. The calculation circuit 14 further calculates the scanning pattern from the converted coordinates (x, y) and outputs the scanning pattern sequentially to the controller 11. In this way, the controller 11 acquires information on the scanning pattern of the optical scanning endoscope 30. As necessary, the calculation circuit 14 displays the acquired scanning pattern of the illumination light on the display apparatus 18. Consequently, the user of the apparatus for setting driving conditions can recognize the scanning pattern on the display apparatus 18. The scanning pattern output to the controller 11 and the scanning pattern displayed on the display apparatus are used in the below-described setting of driving conditions. The controller 11 is configured to store the driving parameters determined to be the driving conditions in the storage 15.

Figure 2:
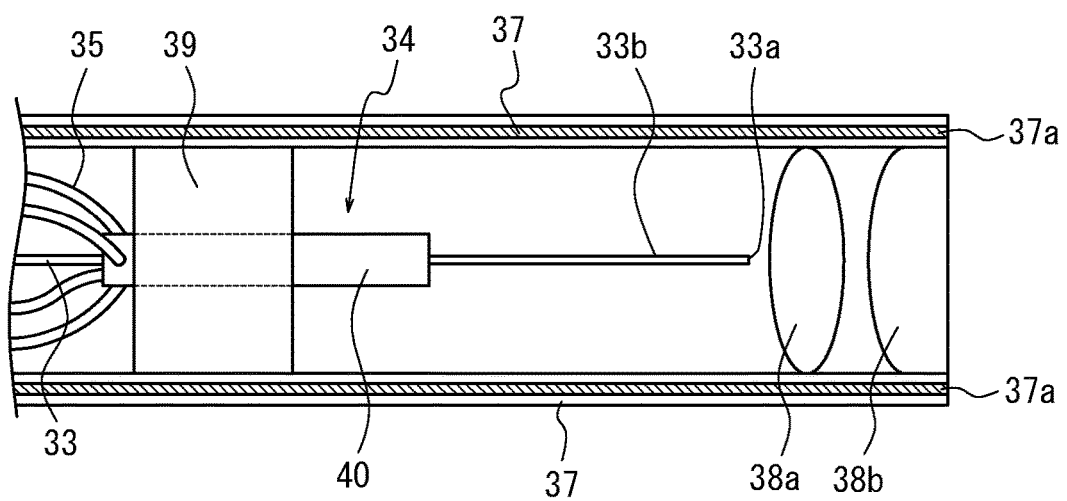
FIG. 2 is a cross-section illustrating the tip of the optical scanning endoscope apparatus in FIG. 1.

Next, the driving mechanism of the optical scanning endoscope 30 is described. FIG. 2 is a cross-section of the tip 32a of an insertion part 32 of the optical scanning endoscope 30 in FIG. 1 (the portion indicated by the dotted line). The tip 32a of the insertion part 32 of the optical scanning endoscope 30 includes the actuator 34, projection lenses 38a and 38b, the optical fiber 33 for illumination that passes through the central portion, and a plurality of optical fibers 37 for receiving light that pass through the peripheral portion. Since the optical fibers 37 for receiving light are used to detect the light to be detected during endoscopic observation and are not used for setting driving conditions, a detailed description thereof is omitted. The actuator 34 includes an actuator tube 40 fixed to the inside of the insertion part 32 by an attachment ring 39, a fiber holding member 41 disposed inside the actuator tube 40, and piezoelectric elements 42a to 42d (see FIGS. 3A and 3B).

The optical fiber 33 for illumination is supported by the fiber holding member 41, and the portion from the fiber holding member 41 to the tip 33a is an oscillating part 33b that is supported vibratably. The projection lenses 38a, 38b are disposed at the extreme end of the insertion part 32. The projection lenses 38a and 38b are configured so that laser light emitted from the tip 33a of the optical fiber 33 for illumination is roughly concentrated on the object for observation. Accordingly, the PSD 20 is positioned so that the light receiving surface matches the position of concentration. The projection lenses are not limited to a double lens structure and may be structured as a single lens or as three or more lenses.

Figure 3A:
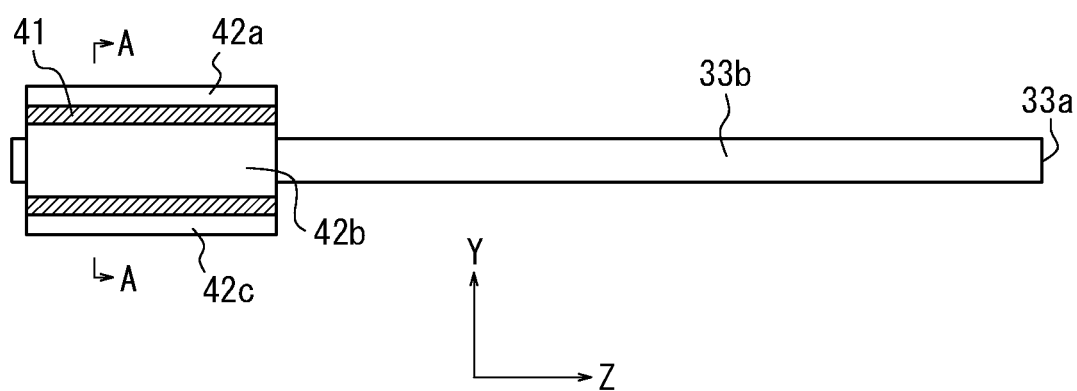
FIGS. 3A and 3B illustrate the actuator of an optical scanning endoscope along with an optical fiber for illumination, where
Figure 3B:
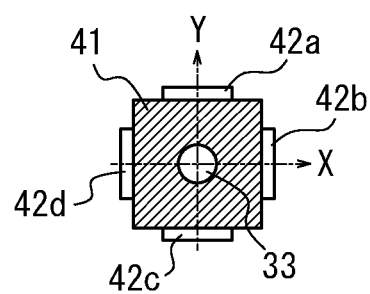

FIGS. 3A and 3B illustrate the actuator 34 of the optical scanning endoscope 30 along with the optical fiber 33 for illumination, where FIG. 3A is a side view, and FIG. 3B is a cross-section along the A-A line in FIG. 3A. The optical fiber 33 for illumination passes through the center of the fiber holding member 41, which has a prismatic shape, and is thereby firmly held by the fiber holding member 41. The four sides of the fiber holding member 41 respectively face the +Y and +X directions and the directions opposite thereto. The +Y and +X directions are perpendicular to the +Z direction that is the emission direction (optical axis direction) at the tip 33a of the optical fiber 33 for illumination and are orthogonal to each other. A pair of piezoelectric elements 42a and 42c for driving in the Y direction are fixed onto the fiber holding member 41 in the +Y direction and the -Y direction, and a pair of piezoelectric elements 42b and 42d for driving in the X direction are fixed in the +X direction and the -X direction. One of the piezoelectric elements 42b and 42d disposed opposite each other with the fiber holding member 41 therebetween expands and the other contracts, thereby causing the fiber holding member 41 to flex. Alternately repeating this operation produces vibration in the X direction. The same is true for vibration in the Y direction as well.

Figure 4:
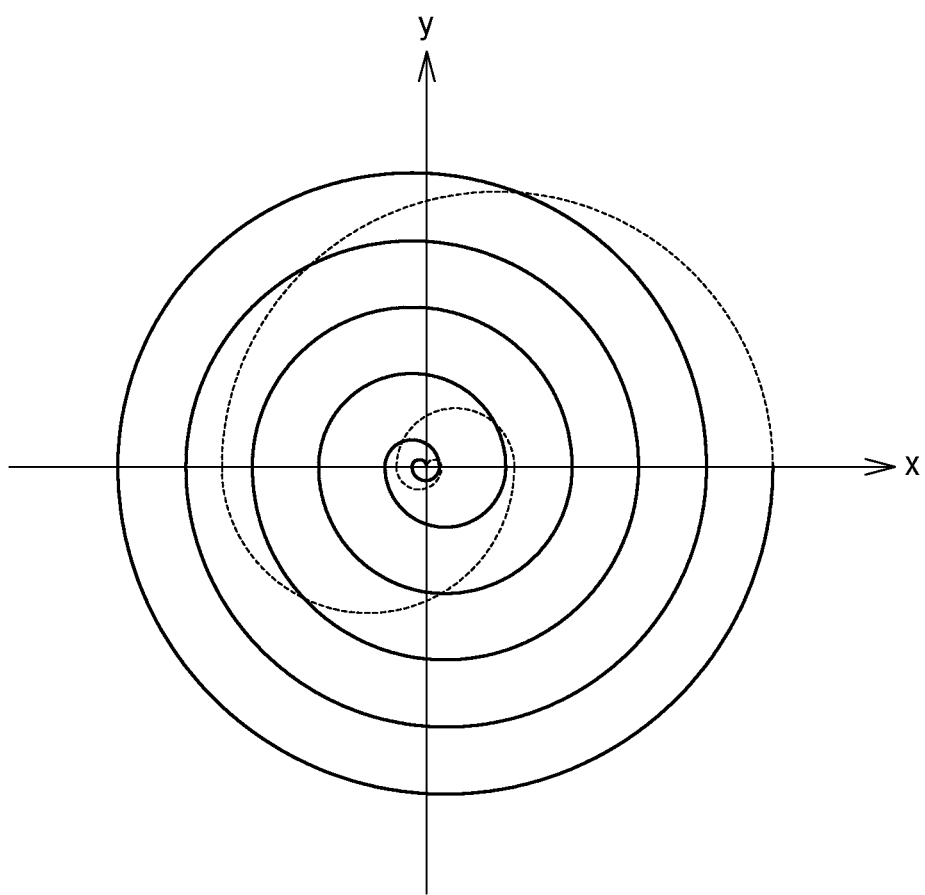
FIG. 4 illustrates a portion of the scanning pattern of a spiral scan.

The drive circuit 13 can perform vibration driving of the piezoelectric elements 42b and 42d for driving in the X direction and the piezoelectric elements 42a and 42c for driving in the Y direction by applying vibration voltage of the same frequency or vibration voltage of different frequencies thereto. Upon vibration driving of the piezoelectric elements 42a and 42c for driving in the Y direction and the piezoelectric elements 42b and 42d for driving in the X direction, the oscillating part 33b of the optical fiber 33 for illumination illustrated in FIGS. 2, 3A, and 3B vibrates, deflecting the tip 33a, so that the laser light emitted from the tip 33a scans the light receiving surface of the PSD 20. A spiral scan can be achieved by applying vibration voltages in the X and Y directions with the same frequency, a phase differing by 90°, and an amplitude that varies between zero and the maximum. Consequently, the light receiving surface of the PSD 20 is scanned so as to draw a spiral pattern such as the one illustrated in FIG. 4. In FIG. 4, the solid curve indicates an example of a scanning pattern when the amplitude increases, whereas the dotted curve indicates an example of a scanning pattern when the amplitude decreases.

Figure 5:
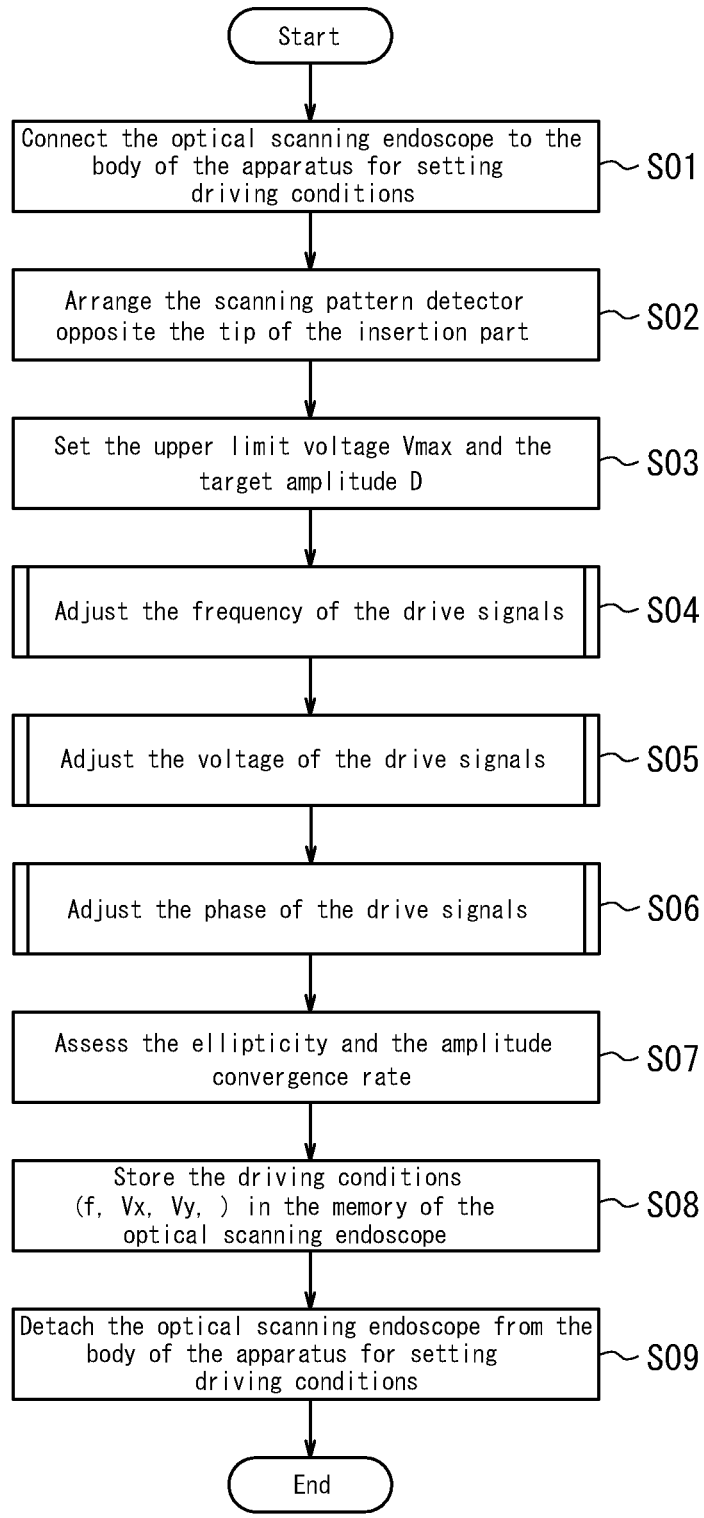
FIG. 5 is a flowchart for setting driving conditions using the apparatus for setting driving conditions in FIG. 1.

Next, a method for setting the driving conditions is described. FIG. 5 is a flowchart for setting driving conditions using the apparatus for setting driving conditions in FIG. 1.

First, the user of the apparatus for setting driving conditions connects the optical scanning endoscope 30 illustrated in FIG. 1 to the body 10 of the apparatus for setting driving conditions (step S01). As a result, the optical fiber 16 for illumination and the drive signal wire 17 of the body 10 of the apparatus for setting driving conditions are respectively connected to the optical fiber 33 for illumination and the drive signal wire 35 of the optical scanning endoscope 30.

Next, the user fixes the tip 32a of the insertion part 32 of the optical scanning endoscope 30 and arranges the PSD 20 so that the light receiving surface of the PSD 20 coincides with the surface of concentrated light where the illumination light irradiated from the tip 32a forms a spot (step S02). The detection signal wire 21 of the PSD 20 is connected to the calculation circuit 14 of the body 10 of the apparatus for setting driving conditions. The PSD 20 is disposed so that while the tip 33a of the optical fiber 33 for illumination of the optical scanning endoscope 30 is not vibrated, the emitted illumination light irradiates the coordinate origin of the PSD 20. Furthermore, the tip 33a of the optical fiber 33 for illumination is driven in only one of the X-direction and the Y-direction, and the coordinate axis direction of the PSD 20 and the direction of linear scanning by the optical fiber 33 for irradiation are caused to coincide. Hence, a mechanism for position adjustment and rotation adjustment of the PSD 20 is preferably provided.

Furthermore, the amplitude Vmax (first drive signal value) of the upper limit voltage applied to the piezoelectric elements 42a to 42d and the target amplitude D are set (step S03). Step S03 corresponds to the step of setting. Upon application of voltage, piezoelectric elements typically deform because of polarization within the crystal. When a voltage large enough to invert the polarization is applied to a piezoelectric element, however, the piezoelectric element may be destroyed, and the polarization may be lost. Therefore, as the voltage applied to the piezoelectric elements 42a to 42d, a maximum value that takes safety into consideration is set. As the target amplitude D, a scanning amplitude for obtaining the desired irradiation range of illumination light is set. The amplitude of the tip 33a of the optical fiber 33 for illumination may be set as the target amplitude, or the amplitude at the irradiation position after passing through the projection lenses 38a and 38b may be set as the target amplitude. In this embodiment, the amplitude is assumed to be set at the irradiation position of the illumination light obtained by the PSD 20. The target amplitude D corresponds to the width of the observable field of view in the case of the optical scanning endoscope 30. The field of view need not be shaped as a true circle and may instead be an ellipse, and the target amplitude D may be changed in the X-direction and the Y-direction.

After step S03, in steps S04 to S06, drive signals are applied to the actuator 34 to vibrate the tip 33a of the optical fiber 33 for illumination, and by adjusting the applied drive signals, the scanning pattern obtained from the PSD 20 is adjusted to become circular. Steps S03 to S06 correspond to the step of adjusting.

First, the frequency of the drive signals is adjusted (step S04). Step S04 corresponds to the step of determining the frequency. Since the adjustment of the frequency of the drive signals is illustrated in detail in the flowchart of the processing to adjust the frequency of the drive signal in FIG. 6, this adjustment is described below with reference to FIG. 6.

First, the resonance frequencies fx, fy of vibration of the optical fiber for illumination are set for each of the X-direction and the Y-direction (step S11). The resonance frequencies fx, fy may be predicted from the design values of the optical scanning endoscope 30 using the finite element method or the like or may be measured in a state of connection to the body 10 of the apparatus for setting driving conditions. In the case of measuring the resonance frequency, vibration voltage is applied from the drive circuit 13 to the actuator 34 individually in the X-direction and Y-direction while changing the frequency. The amplitude of the illumination light emitted from the tip 33a of the optical fiber 33 for illumination can be detected by the PSD 20, and the frequency yielding the maximum amplitude can be determined to be the resonance frequency. Alternatively, a non-illustrated impedance analyzer may be provided in the body 10 of the apparatus for setting driving conditions, and the resonance frequency may be measured by impedance measurement while changing the driving frequency of the optical fiber 33 for illumination. In either case, the voltage applied from the drive circuit 13 to the actuator 34 is set to a sufficiently low value, such as approximately 1/10 of the upper limit voltage Vmax, so as not to damage the optical fiber 33 for illumination even upon vibration at the resonance frequency.

Next, the resonance frequency fx in the X-direction and the resonance frequency fy in the Y-direction are compared (step S12). When fx is greater (the first direction being the Y-direction and the second direction being the X-direction in this case), the frequency is determined by one-dimensional scanning in the Y-direction. First, the driving voltage in the Y-direction is set to Vmax, and the initial value f0 of the driving frequency is set as follows (step S13).

$$f0=fx+\Delta f$$

In other words, f0 is set to exceed the resonance frequency fx in the X-direction by a predetermined frequency $\Delta f$. The frequency $\Delta f$ is preferably ±2% or more of the resonance frequency, for example.

Figure 7:
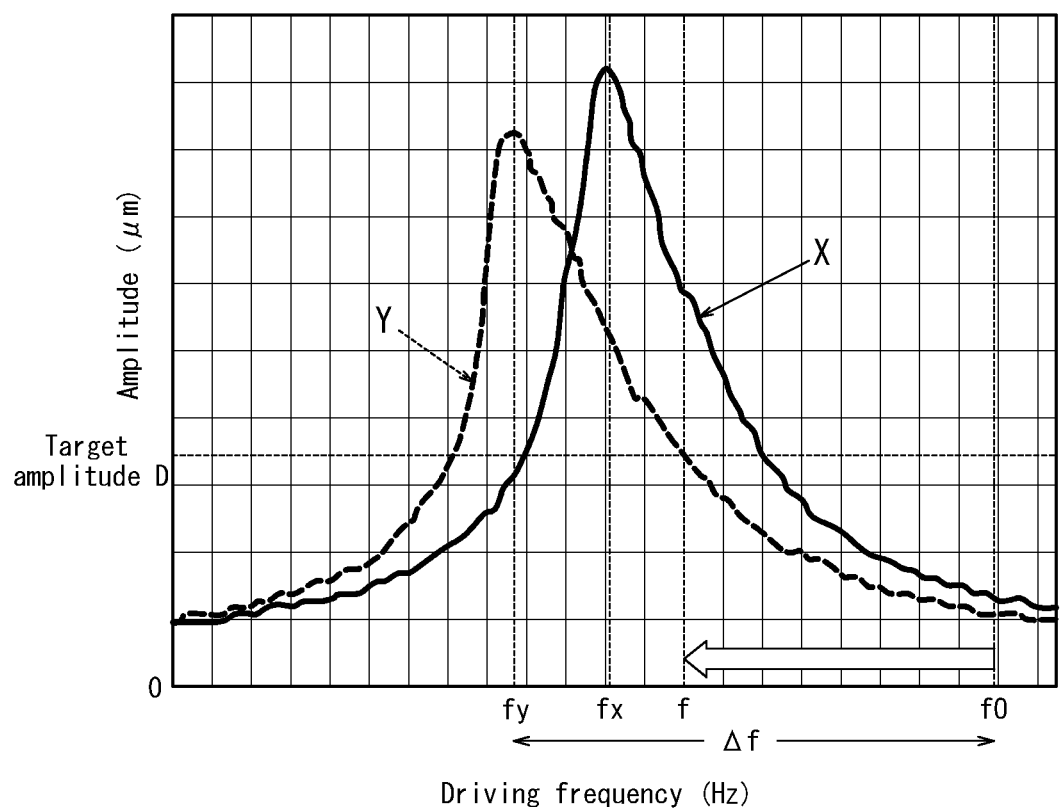
FIG. 7 illustrates an example of frequency characteristics of amplitude in the X-direction and the Y-direction of the tip of the optical fiber.

Next, while causing the light source 12 to emit light, the tip 33a of the optical fiber 33 for illumination is vibrated in the Y-direction by the actuator 34. This state is described with reference to FIG. 7. FIG. 7 illustrates the frequency characteristics of the amplitude in the X-direction and the Y-direction for the same driving voltage. The solid and dashed curves respectively illustrate the change in frequency of the amplitude of the tip 33a of the optical fiber 33 for illumination in the X-direction and the Y-direction. As in the comparison in step S12, the resonance frequency fx in the X-direction is greater than the resonance frequency fy in the Y-direction. The initial value f0 of the driving frequency is set to a frequency sufficiently higher than fx. Under control by the controller 11, the drive circuit 13 sweeps the driving frequency applied for scanning in the Y-direction from the initial value f0 gradually to a low frequency (step S14). At this time, the irradiation position of illumination light is detected by the PSD 20, and the scanning pattern in the Y-direction is calculated by the calculation circuit 14 through the detection signal wire 21. Upon gradually lowering the driving frequency, the scanning amplitude gradually increases to approach the target amplitude D. The controller 11 compares the scanning amplitude with the target value D (step S15). When the scanning amplitude arrives near the target amplitude D, the controller 11 determines the driving frequency f and ends the scan (step S19). "Near the target amplitude D" is, for example, a range of ±10% of the target amplitude D. Within this range of ±10%, a large distortion is not produced even upon expansion or contraction in the X-direction or the Y-direction.

Figure 8:
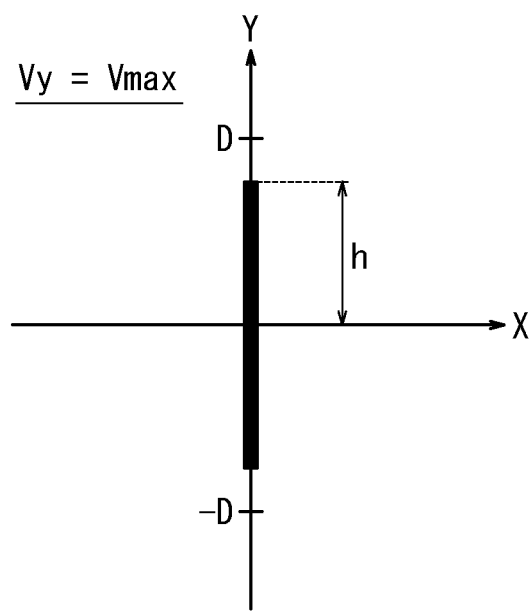
FIG. 8 illustrates the pattern of illumination light in the Y-direction displayed on the display apparatus.

The scanning pattern in the Y-direction can be displayed on the display apparatus 18 as necessary. FIG. 8 illustrates the scanning pattern of illumination light in the Y-direction displayed on the display apparatus 18. The amplitude h of the displayed scanning pattern approaches the target amplitude D as the frequency is reduced. Instead of the driving frequency f being determined by the controller 11, the user may determine the driving frequency f while confirming an image thus displayed on the display apparatus 18. While not indicated in the flowchart in FIG. 6, if the amplitude in the Y-direction does not reach the target amplitude D in step S15 despite reaching the resonance frequency fx in the X-direction upon lowering the driving frequency from f0, steps S16 to S18 below are performed instead. If the amplitude in the Y-direction still does not reach the target amplitude D, the optical scanning endoscope 30 is considered to be defective, and the processing below is suspended.

On the other hand, when the resonance frequency in the X-direction is not greater than the resonance frequency fy in the Y-direction in step S12 (the first direction being the X-direction and the second direction being the Y-direction in this case), the driving voltage Vx in the X-direction is set to Vmax, and the initial value f0 of the driving frequency is set as follows (step S16).

$$f0=fy+\Delta f$$

While scanning from the initial value f0 of the driving frequency in the X-direction, the driving frequency is then swept towards a lower frequency (step S17). When the amplitude in the X-direction arrives near the target amplitude D (step S18), the controller determines the driving frequency f and ends the scan (step S19).

In the above explanation, the initial value f0 of the driving frequency is set to be a higher frequency than the resonance frequencies fx, fy, but the initial value f0 may be set to a lower frequency instead. For example, in the case of fx>fy, the actuator 34 is driven and the tip 33a of the optical fiber 33 tier illumination is scanned in the X-direction with the settings Vx=Vmax and f0=fy−Δf. The frequency is then gradually increased, and the frequency when the amplitude h reaches the target value D can be determined to be the driving frequency f.

Figure 9:
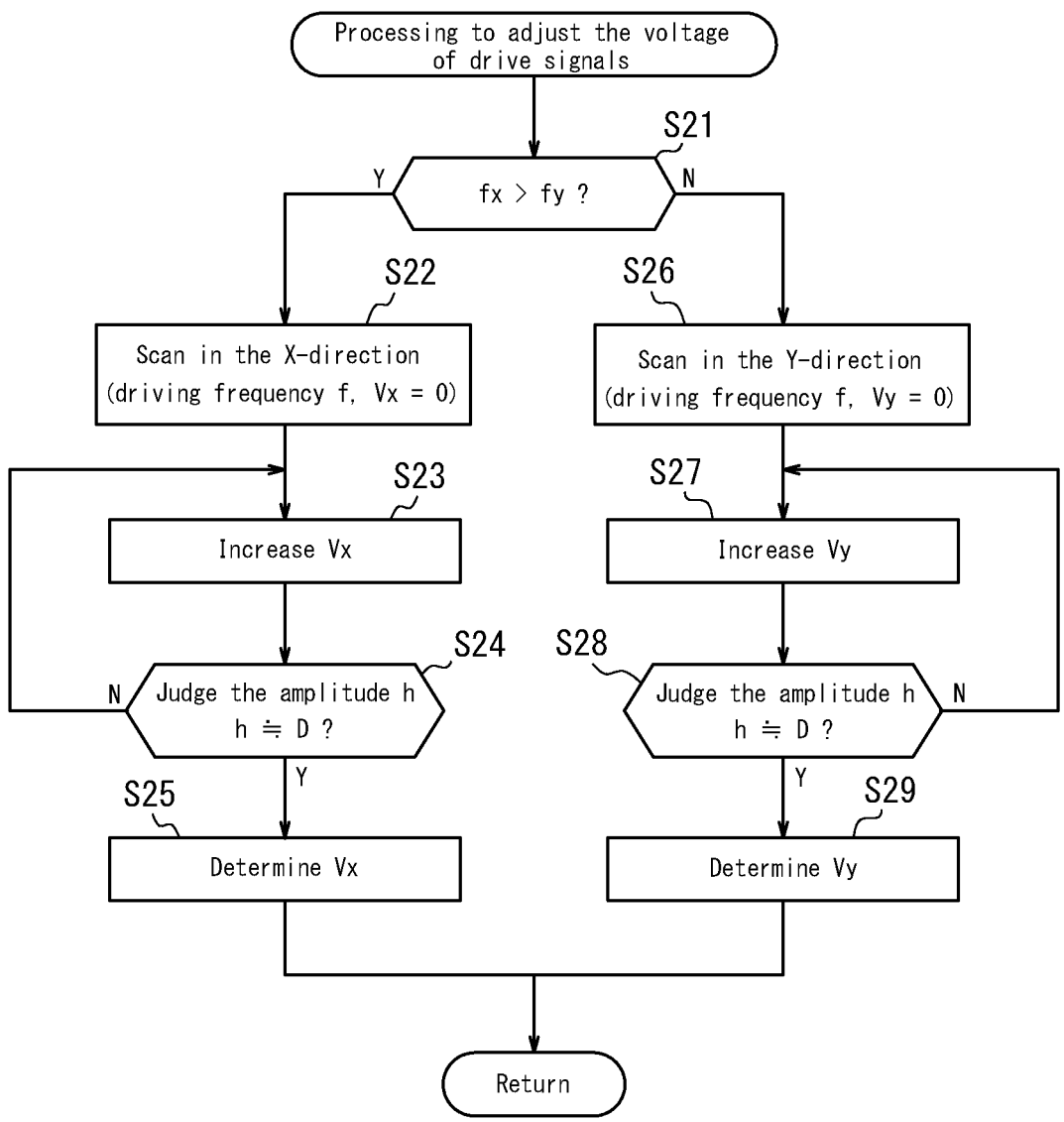
FIG. 9 is a flowchart of processing to adjust the voltage of drive signals.

Next, returning to FIG. 5, the voltage of the drive signals is adjusted (step S05). In the flowchart for adjusting the frequency of the drive signals in FIG. 6, however, the driving voltage in either the X-direction or the Y-direction has already been set to Vmax. In step S05, therefore, the amplitude (second drive signal value) of the other driving voltage that has not yet been determined for the drive signals is determined. Step S05 corresponds to the step of determining the second drive signal value. This processing is described with reference to the flowchart of processing to adjust the voltage of the drive signals in FIG. 9.

Figure 6:
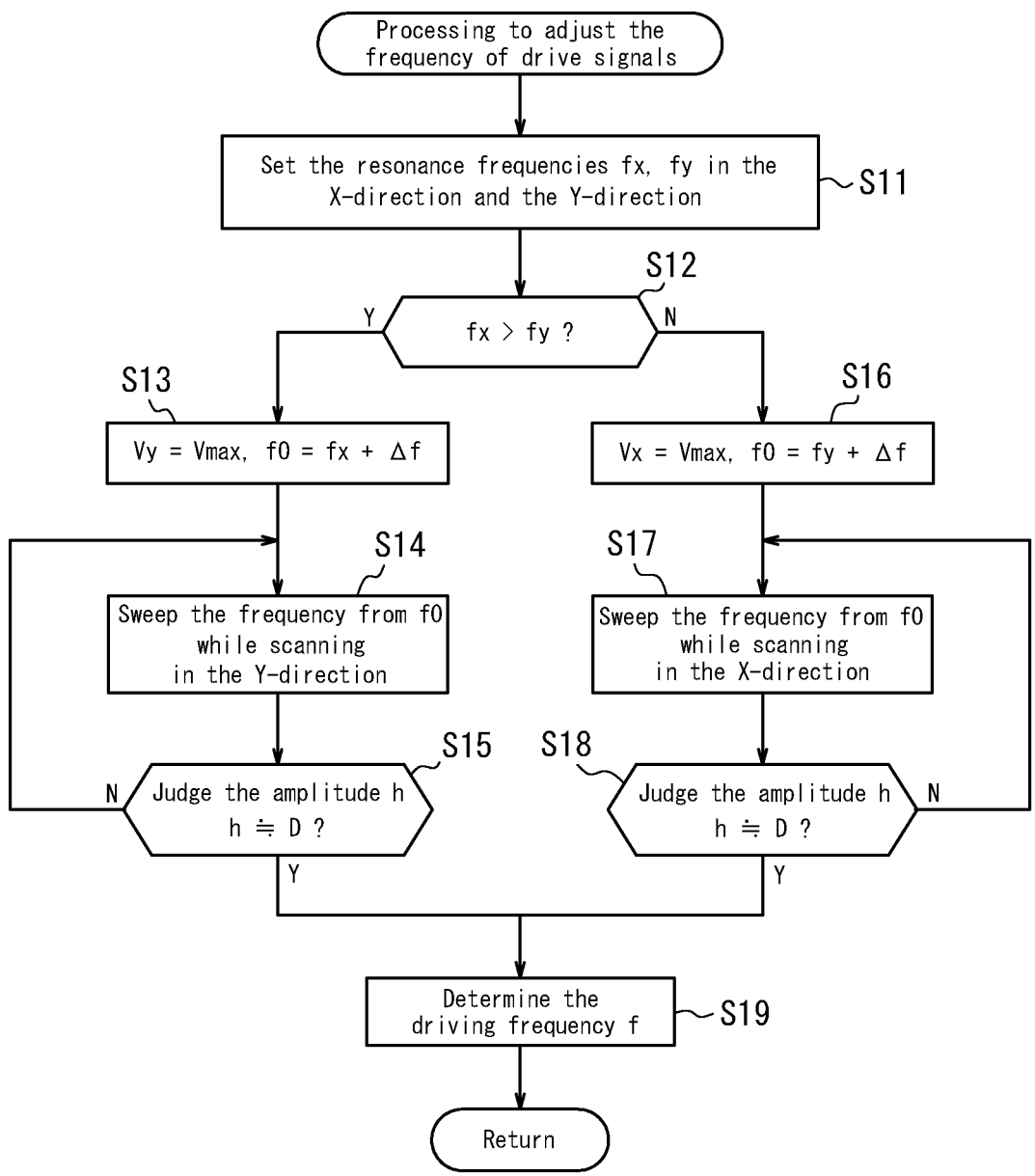
FIG. 6 is a flowchart of processing to adjust the frequency of drive signals.

First, as with the flowchart in FIG. 6, the processing branches on the basis of the magnitude relationship between the resonance frequency fx in the X-direction and the resonance frequency fy in the Y-direction. First, when fx>fy (step S21), the driving voltage Vx in the X-direction (second drive signal value) is determined by steps S22 to S25 below. In this case, the driving voltage Vy in the Y-direction has already been set to Vmax (first drive signal value) in step S13.

First, under control by the controller 11, the light source 12 is caused to emit light, while the drive circuit 13 causes the actuator 34 to scan in the X-direction at the driving frequency f (step S22). The irradiation position of the measurement light is detected by the PSD 20 and calculated by the calculation circuit 14. At this time, the driving voltage Vx is gradually increased from zero (step S23). As a result, the scanning amplitude in the X-direction gradually increases from zero. As illustrated in FIG. 7, when applying the same driving voltage as in the Y-direction (i.e. Vmax), the amplitude of the scanning pattern in the X-direction at the driving frequency f becomes larger than the target amplitude D. Hence, within the range 0<Vx<Vmax, a driving voltage Vx exists such that the amplitude of the scanning pattern becomes the target amplitude D. The determination of the driving voltage Vx in the X-direction is therefore made so that the amplitude of the drive signal does not exceed Vmax (a predetermined value). The controller 11 increases the driving voltage Vx until the scanning amplitude in the X-direction becomes near the target amplitude D, and when determining that the scanning amplitude is near the target amplitude D (step S24), the controller 11 determines the driving voltage Vx to be the value at that time and ends the scan (step S25). Here as well, "near the target amplitude D" is, for example, a range of ±10% of the target amplitude D. The target values in the X-direction and the Y-direction do not need to be the same.

Figure 10:
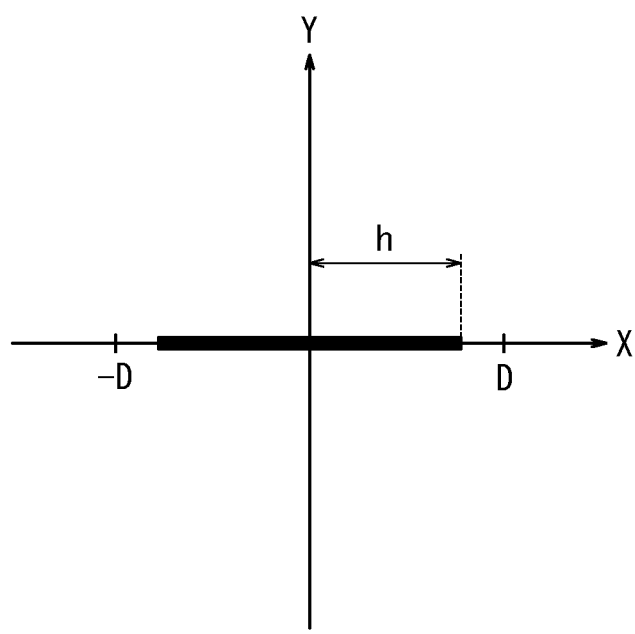
FIG. 10 illustrates the scanning pattern of illumination light in the X-direction displayed on the display apparatus.

The scanning pattern of the measurement light detected by the PSD 20 and calculated by the calculation circuit 14 in steps S22 to S25 is displayed on the display apparatus 18 as necessary. FIG. 10 illustrates the scanning pattern of illumination light in the X-direction displayed on the display apparatus 18. As the driving voltage Vx increases, the scanning amplitude h in the X-direction approaches the target amplitude D. Instead of the driving voltage Vx being determined by the controller 11, the user may determine the driving voltage Vx while confirming an image thus displayed on the display apparatus 18.

In step S21, when it is not the case that fx>fy, the driving voltage Vy in the Y-direction is determined by steps S26 to S29. In this case, the driving voltage Vx in the X-direction is set to Vmax in step S16. First, while causing the light source 12 to emit light, the actuator 34 is driven in the Y-direction at the driving frequency f (step S26). Next, the driving voltage Vy is gradually increased from 0 (step S27), and the scanning amplitude in the Y-direction gradually increases from 0. When determining that the scanning amplitude in the Y-direction is near the target amplitude D (step S28), the controller 11 determines Vy to be the voltage value at that time and ends the scan (step S29). In this case as well, instead of the controller 11 determining the driving voltage Vy, the user may determine the driving voltage Vy while confirming an image displayed on the display apparatus 18.

Next, returning to the flowchart in FIG. 5, the phase of the drive signals is adjusted (step S06). Step S06 corresponds to the step of adjusting the phase. In order to perform an ideal spiral scan, the phase of the driving voltages in the X-direction and the Y-direction applied to the actuator 34 are preferably shifted by 90°. When scanning with actual optical fiber, however, phase shift occurs for reasons such as different delays, between the X-direction and the Y-direction, in the signals from the drive circuit 13 to the actuator 34. It is therefore necessary to adjust the phase of the drive signals.

Figure 11:
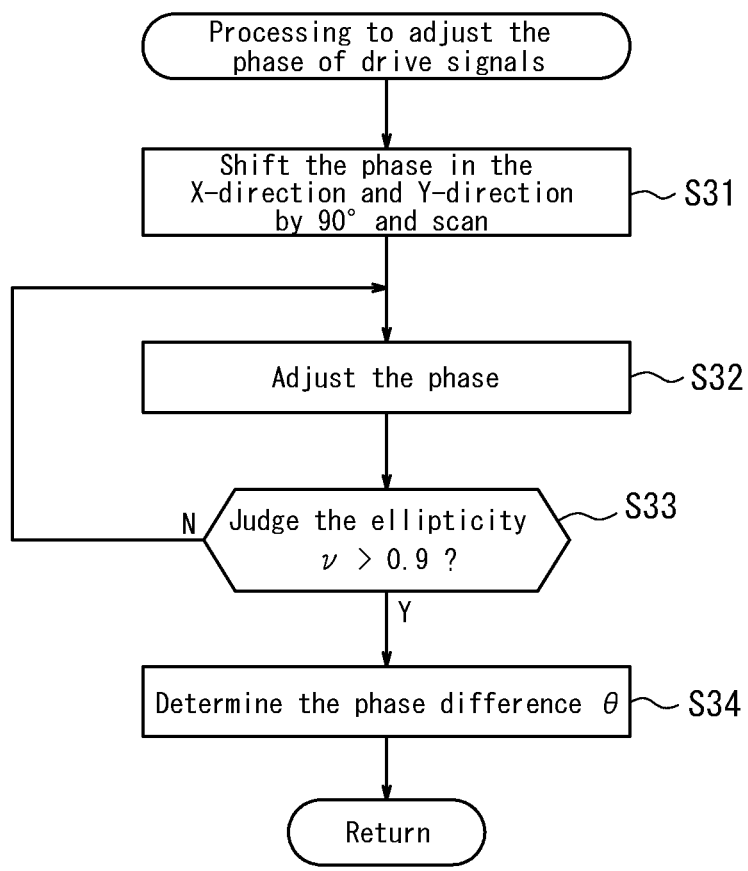
FIG. 11 is a flowchart of processing to adjust the phase of drive signals.

FIG. 11 is a flowchart illustrating processing to adjust the phase of drive signals. First, in the drive circuit 13, the driving frequency and the amplitude of the driving voltages in the X-direction and the Y-direction are set respectively to the frequency f and the driving voltages Vx and Vy determined in steps S04 and S05. Next, drive signals whose phase is shifted by 90° as an initial phase difference are applied to the actuator 34 from the drive circuit 13 (step S31). Ideally, the actuator 34 causes the tip 33a of the optical fiber 33 for illumination to scan over a circular pattern, but the pattern deforms into an ellipse if a phase shift occurs.

Figure 12:
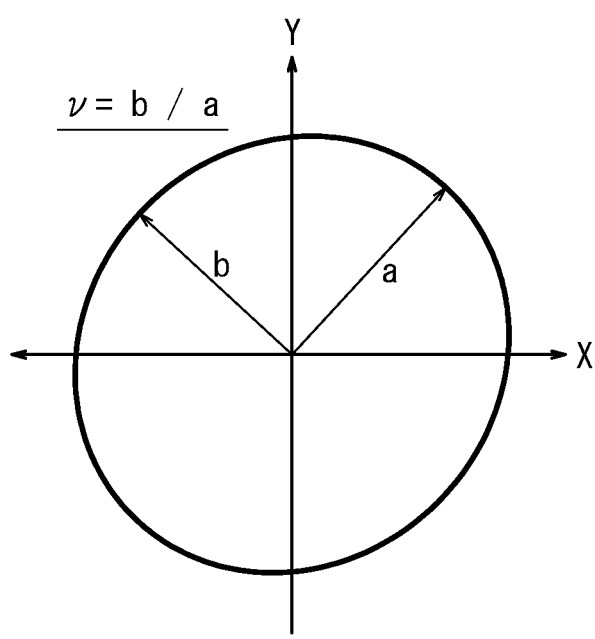
FIG. 12 illustrates an example of an elliptical pattern detected using a PSD.

FIG. 12 illustrates an example of an elliptical pattern detected using the PSD 20. Here, a is the long radius (½ of the length of the major axis) of the ellipse, and b is the short radius (½ of the length of the minor axis). Also, γ as defined by γ=b/a indicates the ellipticity. The controller 11 calculates the ellipticity γ from the scan path calculated by the calculation circuit 14 and adjusts the phase difference of the drive signals in the X-direction and the Y-direction, transmitted from the drive circuit 13 to the actuator 34, so as to bring the scanning pattern closer to a true circle (step S32). This adjustment is made until γ exceeds a predetermined value, for example until the relationship γ>0.9 is satisfied (step S33). In this case, the phase difference upon satisfying γ>0.9 is determined to be the phase difference θ between the drive signals in the X-direction and the Y-direction (step S34). The predetermined value for determining the ellipticity γ is not limited to 0.9 and may also be set to another value. As the value of γ is brought closer to 1, the scanning pattern of the illumination light can be brought closer to a true circle.

In steps S04 to S06 above, the frequency f, the amplitude Vx of the driving voltage in the X-direction, the amplitude Vy of the driving voltage in the Y-direction, and the phase difference θ between the drive signals in the X-direction and the Y-direction are determined as driving parameters for the drive circuit 13. Next, using these driving parameters, a spiral scan is performed, and the ellipticity of the outermost periphery of the scanning pattern and the amplitude convergence rate are assessed (step S07). Step S07 corresponds to the step of testing. Here, the amplitudes Vx, Vy of the driving voltages in the X-direction and the Y-direction are set to the maximum amplitude during the spiral scan.

In steps S04 to S06, the driving parameters for driving the actuator 34 in a circular pattern are determined. When performing spiral scanning, however, distortion may occur in the scanning pattern, and the scanning area may not become circular in some cases. For this reason, a process to confirm the scanning pattern of the spiral scan is performed in step S07. For example, if the ellipticity γ of the outermost periphery of the scanning pattern is smaller than 0.9, the optical scanning endoscope 30 is judged to be defective.

Figure 13A:
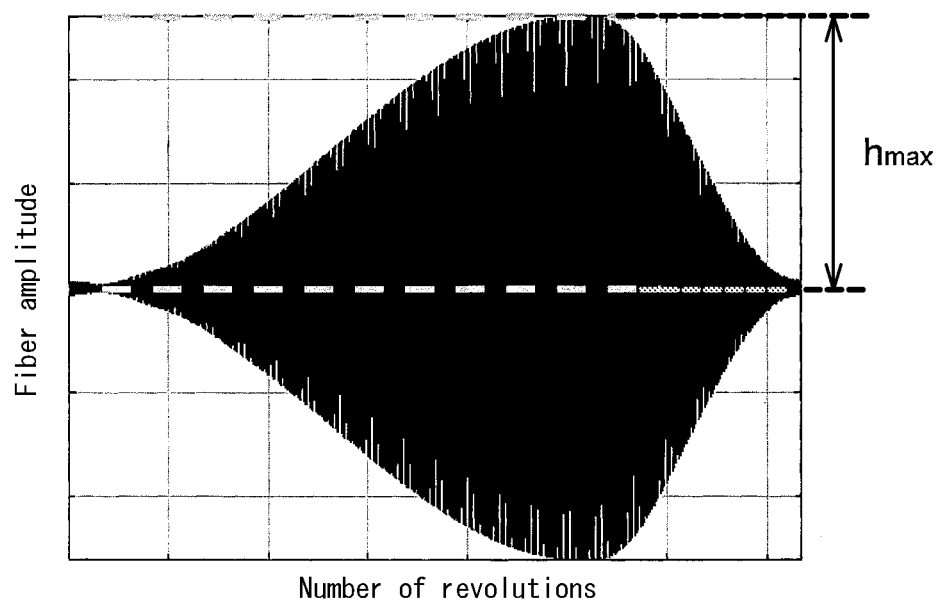
FIGS. 13A and 13B illustrate the amplitude convergence rate of a spiral scan, where
Figure 13B:
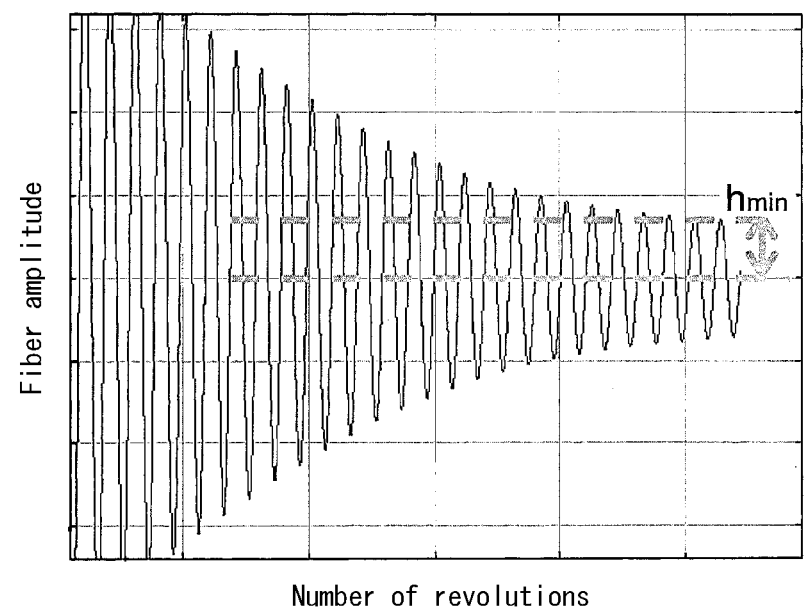

On the other hand, the amplitude convergence rate is an index for assessing the occurrence of an unscanned portion at the center of a scan during spiral scanning and is defined as follows. FIG. 13A illustrates an example of change over time in the scanning pattern in a one-dimensional direction (the X-direction or the Y-direction) in one frame of the spiral scan. FIG. 13B is an expanded view of the scanning pattern in a one-dimensional direction near the minimum value of the amplitude. The amplitude convergence rate is defined as $$h_{min} \div h_{max} \times 100 [\%]$$

where $h_{max}$ is the maximum value and $h_{min}$ is the minimum value of the fiber amplitude during one frame. The maximum radius of the scanning area of the object is associated with the maximum value $h_{max}$ of the amplitude. On the other hand, when the fiber does not attenuate to zero, an unscanned area remains at the central portion of the scanning area. The radius of this area is associated with the minimum value $h_{min}$ of the amplitude. Such an unscanned area leads to the problem of lacking pixel information at the image center.

As compared to an image light guide in which the optical scanning endoscope 30 uses a bundled fiber that can similarly be reduced in diameter, image display that is equivalent to at least 100×100 pixels is preferable in order to obtain excellent effects in terms of resolution. In a 100×100 pixel image, if the above-described amplitude convergence rate is 2%, then pixel information is lacking at the center for 100×0.02=2 pixels. A lack of two pixels or fewer has no serious effect on the resolution upon performing image processing such as pixel interpolation. A greater number of lacking pixels, however, has a serious effect on resolution at the image center. The amplitude convergence rate in the optical scanning endoscope 30 is therefore preferably 2% or less. For example, when the amplitude convergence rate exceeds 2%, the optical scanning endoscope 30 can be judged to be defective.

Next, when the ellipticity and the amplitude convergence rate in appropriate ranges are obtained in step S07, the driving parameters indicating the driving conditions calculated by the calculation circuit 14 either by the controller 11 or by user operation, i.e. the frequency f, the amplitude Vx of the driving voltage in the X-direction, the amplitude Vy of the driving voltage in the Y-direction, and the phase difference θ between the drive signals in the X-direction and the Y-direction, are stored in the memory 36 in the optical scanning endoscope 30 (step S08). Storage in the memory 36 may be accomplished by storing the driving parameters temporarily in the storage 15 of the body 10 of the apparatus for setting driving conditions and then downloading the driving parameters into the memory 36 from the storage 15. Alternatively, a portable storage medium (such as a memory card) removable from the body 10 of the apparatus for setting driving conditions may be mounted onto the storage 15. After calculation of the driving conditions, the user may then remove the storage medium from the body 10 of the apparatus for setting driving conditions and insert the storage medium into a predetermined location on the optical scanning endoscope 30 as the memory 36.

Finally, the user detaches the optical scanning endoscope 30 from the body 10 of the apparatus for setting driving conditions, whereupon setting of the driving conditions is complete (step S09).

In this way, the optical scanning endoscope 30 holds driving parameters in the memory 36. During endoscopic observation using the optical scanning endoscope 30, the optical scanning endoscope 30 is connected to a control apparatus body that includes a light source, a drive circuit, and an image processor, as described above. The control apparatus body reads driving parameters from the memory 36 of the optical scanning endoscope 30 and uses the driving parameters to drive the drive circuit and to operate the actuator 34.

The above process for setting driving conditions may be performed multiple times while changing an environmental condition, and the driving parameters for each different environmental condition may be stored in the memory 36. For example, the temperature condition could be changed to 15° C., 25° C., and 35° C. Alternatively, the driving parameters could be measured while changing the humidity or the pressure state on the tip 32a of the optical scanning endoscope 30. When the optical scanning endoscope 30 is used for actual observation, the driving parameters corresponding to the environmental conditions can be read from the memory 36 in order to set the driving conditions. The driving parameters can also be measured and stored in the memory 36 in accordance with observation conditions such as the zoom state of the optical scanning endoscope 30, i.e. the distance between the tip 33a of the optical fiber 33 for illumination and the projection lenses 38a, 38b.

This disclosure uses the aforementioned apparatus for setting driving conditions to determine driving parameters in accordance with the above-described procedure for setting driving conditions, thereby allowing appropriate driving conditions to be set in the optical scanning apparatus. As a result, the optical scanning endoscope 30 scans at the driving frequency f that is spaced apart from the resonant frequencies fx, fy in the X-direction and the Y-direction so that the amplitude of the scanning pattern becomes the target amplitude D during observation as well, allowing scanning over a desired field of view. Also, since the driving frequency f is spaced apart from the resonant frequencies fx, fy, distortion in the scanning pattern and unscanned portions tend not to occur even upon an environmental change, such as a temperature change, thereby allowing optical scanning over a stable scanning pattern.

Furthermore, setting the driving voltage in the X-direction and the driving voltage in the Y-direction to appropriate voltage values equal to or less than the maximum applied voltage Vmax that takes into account safety of the piezoelectric elements 42a to 42d avoids the application of excessive voltage or current to the actuator 34, which would lead to malfunction or to a shorter lifespan. Also, the driving frequency is determined by gradually approaching the resonance frequency from a frequency that differs from the resonance frequencies fx, fy by a predetermined value, thereby avoiding damage that would be caused by the tip of the optical fiber vibrating at the resonance frequency and the amplitude of the fiber growing too large.

Furthermore, the amplitude of the scanning pattern in each of the X-direction and the Y-direction is adjusted to the target amplitude D, so that even if the structure of the actuator 34 exhibits manufacturing variation, scanning can be performed with the equivalent amplitudes in the directions of two orthogonal axes. The phase is adjusted so that the ellipticity γ becomes larger than a predetermined value, and the phase difference between the X-direction drive signal and the Y-direction drive signal is determined. As a result, the optical fiber 33 for illumination can be scanned over a spiral scanning pattern, the outermost periphery of which is close to a true circle. Furthermore, using the determined driving parameters, the pattern of the spiral scan is assessed to confirm whether the pattern is distorted or unscanned portions have occurred, allowing defects to be recognized.

Since the procedure for determining driving conditions has been defined as an algorithm, the apparatus for setting driving conditions can determine the driving conditions automatically for each optical scanning endoscope 30. Furthermore, the determined driving conditions can be downloaded to the memory internal to the optical scanning endoscope 30 as driving parameters, thereby also automating the setting of the driving conditions in the optical scanning endoscope.

This disclosure is not limited to the above embodiments, and a variety of changes and modifications may be made. For example, the method for driving the optical fiber of the optical scanning apparatus is not limited to a method using piezoelectric elements. The actuator may instead be configured with an electromagnetic driving method that uses coils and a permanent magnet. In this case, the drive circuit controls the current instead of controlling the voltage applied to the actuator.

Furthermore, in the above embodiment, the controller, light source, drive circuit, calculation circuit, and storage are housed in the same body of the apparatus for setting driving conditions, but these components may be separate hardware instead. The above embodiment is applied to setting of driving conditions before shipping an optical scanning apparatus but may instead be applied to adjustment of driving conditions of an optical scanning apparatus already in use. Furthermore, in the above embodiment, the body of the apparatus for setting driving conditions is provided separately from the control apparatus body for endoscopic observation, but instead, the functions of the body of the apparatus for setting driving conditions may be embedded within the control apparatus body for endoscopic observation, and the user may be allowed to adjust the driving conditions by connecting a PSD.

While the scanning pattern detector has been described as the PSD, use is not limited to a PSD. For example, an image sensor such as a CCD may be disposed at the position of concentration of light from the scanning apparatus. Alternatively, a screen may be disposed at the irradiation position of illumination light, and by visually confirming the scanning pattern of illumination light observed on the screen, the user may operate the input apparatus to set the various driving parameters.

Although the target amplitude in the above embodiment has been described as the amplitude of the scanning pattern detected on the PSD light receiving surface, the target amplitude may instead be the value yielded by dividing the amplitude of the scanning pattern by the magnification of the projection optical system. In this case, the target amplitude becomes the amplitude of the optical fiber tip. Adjustment of the driving voltage to bring the scanning amplitude closer to the target amplitude may be accomplished by, for example, adjusting the gain of a voltage amplifier in the driving circuit. Similarly, when using an electromagnetic driving method, the driving current can be adjusted by adjusting the gain of a current amplifier.

The optical scanning apparatus is not limited to an optical scanning endoscope and may also be applied to an optical scanning microscope or an optical scanning projector that scans with a fiber. In the above embodiments, the optical scanning endoscope that is an optical scanning apparatus does not include a light source and a drive circuit, but this disclosure may also be applied to an optical scanning apparatus that incorporates these components. In this case, the apparatus for setting driving conditions at least includes a controller for the body of the apparatus for setting driving conditions, which is connected to the optical scanning apparatus; a scanning pattern detector; and a storage apparatus that stores position information detected by the scanning pattern detector. Under control by the controller, the light source of the optical scanning apparatus and the drive circuit are driven to scan with the fiber, the position of the optical spot is detected by a PSD, the driving conditions are set, and the driving parameters are stored in the storage apparatus. A variety of other modifications may also be made to the configuration of the apparatus for setting driving conditions.

INDUSTRIAL APPLICABILITY

The apparatus for setting driving conditions and the method for setting driving conditions according to this disclosure may be suitably used for example to set driving conditions before shipping an optical scanning apparatus.

REFERENCE SIGNS LIST

10 Body of apparatus for setting driving conditions
11 Controller
12 Light source
13 Drive circuit
14 Calculation circuit
15 Storage
16 Optical fiber for illumination
17 Drive signal wire
18 Display apparatus
19 Input apparatus
20 PSD
21 Detection signal wire
30 Optical scanning endoscope
31 Connector
32 Insertion part
32a Tip
33 Optical fiber for illumination
33a Tip
33b Oscillating part
34 Actuator
35 Drive signal wire
36 Memory
37 Optical fibers for receiving light
37a Tip
38a, 38b Projection lens
39 Attachment ring
40 Actuator tube
41 Fiber holding member
42a, 42b, 42c, 42d Piezoelectric element

The invention claimed is:

1. A method for setting driving conditions applied in an optical scanning apparatus comprising an optical fiber that guides light from a light source and emits the light from a tip supported vibratably and an actuator that vibrates the tip of the optical fiber, the method comprising:
attaching a scanning pattern sensor configured to detect a scanning pattern of the light emitted from the tip of the optical fiber; and
adjusting the scanning pattern detected by the scanning pattern sensor by applying a drive signal to the actuator to vibrate the tip and changing the drive signal,
wherein the adjusting comprises:
setting a first drive signal value of the drive signal applied to the actuator and a target amplitude of the scanning pattern; and
determining a frequency of the drive signal applied to the actuator by comparing an amplitude of the scanning pattern detected by changing the frequency of the drive signal applied to the actuator with the target amplitude while vibrating the actuator at the first drive signal value;
wherein the actuator is configured to be capable of vibrating the optical fiber in a first direction and a second direction that are orthogonal to each other and are orthogonal to an emission direction of the light at the tip of the optical fiber, the method further comprising determining, after the frequency of the drive signal is determined for vibration in the first direction in the determining of the frequency, a second drive signal value applied to the actuator by comparing an amplitude of the scanning pattern detected by changing the drive signal applied to the actuator in the second direction with the target amplitude while vibrating the actuator in the second direction at the determined frequency; and
the adjusting further comprises adjusting phase by adjusting a phase difference, after the determining of the second drive signal value, between a drive signal in the first direction and a drive signal in the second direction so that an ellipticity γ=b/a exceeds a predetermined value, where a is a long radius and b is a short radius of a peripheral shape of the scanning pattern detected by the scanning pattern sensor when, at the determined frequency, a drive signal at the first drive signal value is applied to the actuator in the first direction and a drive signal at the second drive signal value is applied to the actuator in the second direction.

2. The method for setting driving conditions of claim 1, wherein in the determining of the frequency, the frequency of the drive signal applied to the actuator is changed towards a resonance frequency of the tip of the optical fiber from an initial value that is a frequency separated from the resonance frequency by a predetermined value.

3. The method for setting driving conditions of claim 1, wherein the determining of the second drive signal value is performed so that an amplitude of the drive signal in the second direction does not exceed a predetermined value.

4. The method for setting driving conditions of claim 1, b is the short radius of an outermost peripheral shape of the scanning pattern detected by the scanning sensor and at the determined frequency, a drive signal taking the first drive signal value as a maximum value of amplitude is applied to the actuator in the first direction and a drive signal taking the second drive signal value as a maximum value of amplitude is applied to the actuator in the second direction to cause the tip of the optical fiber to scan in a spiral.

5. The method for setting driving conditions of claim 1, further comprising testing an amplitude convergence rate after the phase adjusting, the amplitude convergence rate being a value obtained by dividing a minimum amplitude by a maximum amplitude of the scanning pattern detected by the scanning pattern sensor when applying a drive signal to the actuator to cause the tip of the optical fiber to scan in a spiral, the drive signal taking the first drive signal value as a maximum value of amplitude in the first direction and taking the second drive signal value as a maximum value of amplitude in the second direction.

6. The method for setting driving conditions of claim 4, further comprising testing an amplitude convergence rate after the phase adjusting, the amplitude convergence rate being a value obtained by dividing a minimum amplitude by a maximum amplitude of the scanning pattern detected by the scanning pattern sensor when applying a drive signal to the actuator to cause the tip of the optical fiber to scan in a spiral, the drive signal taking the first drive signal value as a maximum value of amplitude in the first direction and taking the second drive signal value as a maximum value of amplitude in the second direction.

7. The method for setting driving conditions of claim 1, further comprising storing, in a memory of the optical scanning apparatus, the frequency of the drive signal determined frequency, the set first drive signal value, the set second drive signal value, and the phase difference adjusted in the phase adjusting.

8. The method for setting driving conditions of claim 4, further comprising storing, in a memory of the optical scanning apparatus, the frequency of the determined drive signal, the set first drive signal value, the set second drive signal value, and the phase difference adjusted in the phase adjusting.

9. The method for setting driving conditions of claim 1, wherein the optical scanning apparatus is an optical scanning endoscope.

10. An apparatus for setting driving conditions applied in an optical scanning apparatus comprising an optical fiber that guides light from a light source and emits the light from a tip supported vibratably and an actuator that vibrates the tip of the optical fiber, the apparatus for setting driving conditions comprising:
a controller configured to control the actuator; and
a scanning pattern sensor configured to detect a scanning pattern of the light emitted from the tip of the optical fiber, wherein
the controller adjusts the scanning pattern detected by the scanning pattern sensor by applying a drive signal to the actuator to vibrate the tip and changing the drive signal, the controller adjusting the scanning pattern by setting a first drive signal value of the drive signal applied to the actuator and a target amplitude of the scanning pattern and then determining a frequency of the drive signal applied to the actuator by comparing an amplitude of the scanning pattern detected by changing the frequency of the drive signal applied to the actuator with the target amplitude while vibrating the actuator at the first drive signal value;
wherein the actuator is configured to be capable of vibrating the optical fiber in a first direction and a second direction that are orthogonal to each other and are orthogonal to an emission direction of the light at the tip of the optical fiber, and the controller is configured to, after determining the frequency of the drive signal for vibration in the first direction, determine a second drive signal value applied to the actuator by comparing an amplitude in the second direction of the scanning pattern detected by changing the drive signal applied to the actuator in the second direction with the target amplitude while vibrating the actuator in the second direction at the determined frequency; and the controller is configured to, after determining the second drive signal value, adjust a phase difference between a drive signal in the first direction and a drive signal in the second direction so that an ellipticity $\gamma=b/a$ exceeds a predetermined value, where a is a long radius and b is a short radius of a peripheral shape of the scanning pattern detected by the scanning pattern sensor when, at the determined frequency, a drive signal at the first drive signal value is applied to the actuator in the first direction and a drive signal at the second drive signal value is applied to the actuator in the second direction.

11. The apparatus for setting driving conditions of claim 10, wherein the controller determines the frequency of the drive signal applied to the actuator by changing the frequency of the drive signal applied to the actuator towards a resonance frequency of the tip of the optical fiber from an initial value that is a frequency separated from the resonance frequency by a predetermined value.

12. The apparatus for setting driving conditions of claim 10, wherein b is the short radius of an outermost peripheral shape of the scanning pattern detected by the scanning pattern and at the determined frequency, a drive signal taking the first drive signal value as a maximum value of amplitude is applied to the actuator in the first direction and a drive signal taking the second drive signal value as a maximum value of amplitude is applied to the actuator in the second direction to cause the tip of the optical fiber to scan in a spiral.

13. The apparatus for setting driving conditions of claim 10, wherein the controller is configured to, after adjusting the phase difference, test an amplitude convergence rate that is a value obtained by dividing a minimum amplitude by a maximum amplitude of the scanning pattern detected by the scanning pattern sensor when applying a drive signal to the actuator to cause the tip of the optical fiber to scan in a spiral, the drive signal taking the first drive signal value as a maximum value of amplitude in the first direction and taking the second drive signal value as a maximum value of amplitude in the second direction.

14. The apparatus for setting driving conditions of claim 12, wherein the controller is configured to, after adjusting the phase difference, test an amplitude convergence rate that is a value obtained by dividing a minimum amplitude by a maximum amplitude of the scanning pattern detected by the scanning pattern sensor when applying a drive signal to the actuator to cause the tip of the optical fiber to scan in a spiral, the drive signal taking the first drive signal value as a maximum value of amplitude in the first direction and taking the second drive signal value as a maximum value of amplitude in the second direction.

15. The apparatus for setting driving conditions of claim 10, wherein the apparatus for setting driving conditions stores, in a memory of the optical scanning apparatus, the frequency of the drive signal, the first drive signal value, the second drive signal value, and the phase difference.

16. The apparatus for setting driving conditions of claim 12, wherein the apparatus for setting driving conditions stores, in a memory of the optical scanning apparatus, the frequency of the drive signal, the first drive signal value, the second drive signal value, and the phase difference.

* * * * *